(12) United States Patent
Blum et al.

(10) Patent No.: US 9,155,916 B2
(45) Date of Patent: *Oct. 13, 2015

(54) COSMETIC PREPARATION AND METHOD FOR PREPARING THE SAME

(71) Applicant: Mibelle AG, Buchs (CH)

(72) Inventors: Peter Blum, Richterswil (CH); Cornelia Schurch, Lenzburg (CH); Daniel Schmid, Brugg (CH); Fred Zulli, Kuttigen (CH)

(73) Assignee: Mibelle AG, Buchs (CH)

( * ) Notice: Subject to any disclaimer, the term of this patent is extended or adjusted under 35 U.S.C. 154(b) by 99 days.

This patent is subject to a terminal disclaimer.

(21) Appl. No.: 14/075,777

(22) Filed: Nov. 8, 2013

(65) Prior Publication Data

US 2014/0072619 A1    Mar. 13, 2014

Related U.S. Application Data

(63) Continuation of application No. 12/148,241, filed on Apr. 17, 2008, now abandoned, and a continuation of application No. 13/443,995, filed on Apr. 11, 2012, now Pat. No. 8,580,320.

(30) Foreign Application Priority Data

Apr. 27, 2007   (CH) ...................................... 0701/07

(51) Int. Cl.

| | |
|---|---|
| *A61K 8/02* | (2006.01) |
| *A61K 36/00* | (2006.01) |
| *A61K 36/73* | (2006.01) |
| *A61Q 19/10* | (2006.01) |
| *A61K 8/14* | (2006.01) |
| *A61K 8/97* | (2006.01) |
| *A61Q 5/00* | (2006.01) |
| *A61Q 7/00* | (2006.01) |
| *A61Q 19/00* | (2006.01) |
| *A61Q 19/08* | (2006.01) |
| *A61K 9/06* | (2006.01) |
| *A61K 9/107* | (2006.01) |
| *A61K 9/113* | (2006.01) |
| *A61K 9/127* | (2006.01) |

(52) U.S. Cl.

CPC . *A61Q 19/10* (2013.01); *A61K 8/14* (2013.01); *A61K 8/97* (2013.01); *A61K 36/00* (2013.01); *A61Q 5/00* (2013.01); *A61Q 7/00* (2013.01); *A61Q 19/00* (2013.01); *A61Q 19/08* (2013.01); *A61K 9/06* (2013.01); *A61K 9/107* (2013.01); *A61K 9/113* (2013.01); *A61K 9/127* (2013.01)

(58) Field of Classification Search
CPC ....... A61K 2300/00; A61K 8/97; A61K 8/14; A61K 36/736; A61K 36/73
See application file for complete search history.

(56) References Cited

U.S. PATENT DOCUMENTS

| | | |
|---|---|---|
| 5,643,598 A | 7/1997 | Meybeck |
| 6,555,118 B1 | 4/2003 | Niazi |
| 2005/0265953 A1 | 12/2005 | Ennamany et al. |

FOREIGN PATENT DOCUMENTS

| | | |
|---|---|---|
| EP | 1064932 A1 | 3/2001 |
| EP | 1174120 A1 | 1/2002 |
| FR | 25434487 A1 | 4/1984 |
| JP | 3277219 A1 | 12/1991 |
| JP | 7711090 A1 | 12/1991 |
| WO | 01/47538 A1 | 7/2001 |
| WO | 03/077881 A2 | 9/2003 |
| WO | 2005/072697 A1 | 8/2005 |

OTHER PUBLICATIONS

Fuchs et al. (2004) Cell, vol. 116, 769-778.*
Nohynek et al. (2007) Crit. Rev. Tox. 37, 251-277.*
Weigel, D. and Juergens, G. (2002) Stem Cells That Make Stems, Nature, vol. 415, pp. 751-754.
EPO Search Report for priority application CH 7012007.

* cited by examiner

*Primary Examiner* — Chris R Tate
*Assistant Examiner* — Russell Fiebig
(74) *Attorney, Agent, or Firm* — Maginot, Moore & Beck, LLP

(57) ABSTRACT

The present invention relates to the use of dedifferentiated plant cells in cosmetic preparations for protecting of stem cells against intrinsic and extrinsic stress factors, in particular for promoting proliferation of stem cells and for protecting them against apoptosis. In particular, the invention relates to the use of dedifferentiated plant cells from fruits of *Malus domestica* (Apple) cultivar *Uttwiler Spaetlauber*. Further, the invention relates to a method for cultivating of dedifferentiated plant cells, as well as to the preparation of extracts of plant cell cultures which are suitable for such applications.

6 Claims, 5 Drawing Sheets

Control          0.1% Extract

COSMETIC PREPARATION AND METHOD FOR PREPARING THE SAME

REFERENCE TO RELATED APPLICATION

The present application is a continuation of and claims priority to co-pending application Ser. No. 13/443,995, which was filed on Apr. 11, 2012, which in turn is a continuation of application Ser. No. 12/148,241, which was filed on Apr. 17, 2008, the disclosures of which are incorporated herein by reference in their entirety.

FIELD OF INVENTION

The present invention relates to the use of dedifferentiated plant cells in cosmetic preparations for protecting of stem cells against intrinsic and extrinsic stress factors, in particular for promoting proliferation of stem cells and for protecting them against apoptosis. In particular, the invention relates to the use of dedifferentiated plant cells from fruits of *Malus domestica* (Apple) cultivar *Uttwiler Spaetlauber*. Further, the invention relates to a method for cultivating of dedifferentiated plant cells, as well as to the preparation of extracts of plant cell cultures which are suitable for such applications.

BACKGROUND OF THE INVENTION

Stem cells (SC) are uniform undifferentiated cells having the property of constant regeneration and the unique ability of turning into any other cell type by cleavage and differentiation. By said potential, SC are a renewable source of human tissue. Thus, SC be-came an important object of medical research for various applications, such as gene therapy, organ transplantation, diabetes, and plastic surgery.

SC may be divided into two groups, i.e. embryonic and adult (EC). Embryonic stem cells play a key role in the first development phase of an organism. They are able to endlessly cleave and to develop every necessary type of tissue. Thus, they are able to form from a single cell a whole body, either the plant or the animal form which they originate. Due to this ability they are also called pluripotent cells. Unfortunately, for human beings this ability is restricted to the embryonal phase. In later phases of life of a subject EC are no longer present.

The second type of stem cells are adult stem cells. So far, these cells could be identified in many full-grown tissues and organs, such as bone marrow, pancreas, spine, brain, central nervous system, peripheral blood, dental pulp, blood vessel, skeletal muscles, cornea, retina, liver, cord blood, heart, epithelium of the intestinal tract, and dermis.

Compared with EC adult SC derived from such tissues have only a limited choice of differentiation. Some of them can only differentiate into one single tissue type mostly the one which is surrounding them. Thus, they are called unipotent SC. Other SC can differentiate into various tissue types and therefore are called multipotent.

Both types of adult SC are promising for medical applications since they are more easily accessible and their recovery is ethically less problematical than of ES. A survey on SC and their possibilities may be gleaned in Lemoni et al., 2005, Stem Cell Plasticity: Time for a Reappraisal, Hematologica/The Hematology Journal, 90 (3), 360 to 381.

The skin of mammals is a multilamina system which is continuously revolving. The part which is constantly in contact with the outside world is called epidermis. The major task of this specialized Tissue is to protect the body against dehydration, lesions and infections. It is composed four different laminas which are all formed by a single cell type, the so-called cerationocytes. Whereas this cell type is not much differentiated, is nevertheless has its origin in specialized skin stem cells. They are located in the lowermost lamina of the epidermis, the basal lamina.

In several papers successful isolation of such skin stem cells is reported. It even could be demonstrated that skin stem cells may be found in lower tissues of the skin, i.e. in the so-called hair follicle bulge. Contrary to the SC in the basal lamina these SC are multipotent, i.e. they are able to differentiate into every tissue type of the skin. A survey may be gleaned in: Roh et al., 2006, Cutaneous Stem Cells and Wound Healing, Pediatric Research, 59 (4), Pt 2, 100 to 103R; Morasso et al., 2005, Epidermal Stem Cells; The Cradle of Epidermal Determination, Differentiation and Wound Healing, Biol. Cell., 97, 173 to 183; and Alonso et al., 2003, Colloquium: Stem Cells of the Skin Epithelium, PNAS, 100, Suppl. 1, 11830 to 11835.

Skin stem cells are crucial in the wound healing and the regeneration of skin and hair. However, the capacity of these abilities may be disturbed by genetic problems, environmental influences and the aging process. Thus, protection of these SC is extremely important. Therefore, as will be explained below more in detail, it was an object of the present invention to develop a plant extract able to protect and stimulate these SC in cosmetic preparations.

Plant extracts and the use of parts of plants, such as leaves, fruits, flowers, stems, bark, inflorescences and roots for cosmetic and medical Applications are known since ancient times. Products derived therefrom may be, e.g., essential oils, fibers, starch, flavors, coloring matters, antibiotics, proteins, phenols, acids or fats. The use of plants or plant extracts in cosmetics is rampant. There are a great many of different uses, such as humidification, brighteners, tanning lotions, make-ups, sun filters, scavengers, antioxidants, immunity stimulation, detergents, preserving agents or thickening agents.

Examples of recently found uses are described in: KR20040091178, KR20040059007, US20062400129, WO2006099930, WO2006086707, US2006153792, JP2006151934, WO2006068777, WO2006053761, WO2006008418, LV13345, UA73556, CN1679498, and many others.

The spectrum of useful plants and plant component is wide and comprises e.g. algae, succulents, berries, carnivorous plants, herbs, cereals and trees. Usual well known examples of plants, however not limited to them, are: *Spirulina* algae, aloe vera, calendula, ginkgo, ginseng, iris, valerian, sage, lavender, thyme, peppermint, Saint-John's-wort, citrons, peach, guava, avocado, wheat, and oat.

However there are restrictions with respect to the use of plants or plant components. i.e.:

The availability may be restricted, e.g. by the seasons, limited storage capacities, protection of species, problems in cultivation, or bad harvests.

The quality is not unchanging, e.g. due to seasonal variations, different cultivation methods, geographic differences, different suppliers, clones, pollution of the environment, or physical status.

These facts often make the use of plants in cosmetic applications impossible.

Therefore, the utilization of methods of plant cell culture techniques may help to solve such problems. Said utilization comprises techniques which allow, when observing certain known process steps, to obtain uniform dedifferentiated cells, showing the following advantages as compared with cultivated whole plants:

Independency from seasons;
Continuous production:
Freedom from pollution of environment and other impurities;
With respect to quantity and quality manageable and reproducible production of metabolites;
Protection of rare or limited plant reserves;
No limitation of market availability.

Examples for the use of plant cell cultures of various species, their cultivation and their use in cosmetic preparations may e.g. be found in: EP1244464, FR2837385, US2006021084, WO2005108596, WO2005070066.

The basic principle of cultivation of such dedifferentiated plant cells utilizes the biological fact, that every plant cell has the ability to build up the whole plant which the cell stems from. This ability is called totipotency and is comparable with the pluripotency of animal ES. Therefore, it may be accepted that dedifferentiated plant cells do have a positive influence on protection and activation of skin stem cells.

In order to achieve this effect various dedifferentiated plant cells can be used. However, further supplemental useful effects can be achieved using these plant extract as well. An investigation within several plant groups showed that apples and fruits belonging to the subfamily Maloideae of the family of Rosaceae are much promising. A known exponent of this family is the cultivated apple tree (*Malus domestica*). Apples have a long tradition in cosmetic applications. Originally, they were applied in the form of masks of pressed pulp or peelings which provided moisture and tautness of the skin. Another application is the use of apple aromas and extracts in all kinds of cosmetic preparation, such as e.g. shampoos, lotions, soaps, bath essences or toothpastes.

The main ingredients of apples are various sugars, vitamins, acids, oils, waxes and polyphenols. Recently published studies could prove that especially the overall polyphenols in apple extracts or apple juices rich in polythenols can be useful in preventing and combating colon cancer (Eberhart et al., 2000, Antioxidant Activity of Fresh Apples, Nature, 405, 903 to 904; Liu et al., 2003, Antiproliferative Activity of Apples is not due to Phenolic-induced Hydrogen Peroxide Formation, J. Agric. Food Chem., 51, 1718 to 1723; Kern et al., 2005, Inhibitors of the Epidermal Growth Factor Receptor in Apple Juice Extract, Mol. Nutr. Food Res., 49, 317 to 328). Thereby, to a certain extent, the juices rich in polyphenols had an influence on the Wnt-pathway. This pathway is a cytobiological signaling cascade in which β-catenin is the main protein. Under normal circumstances, this protein is present in the cell on a constant level. If this level is disturbed, as in a cancer cell, the β-catenin level rises, and the β-catenin is transported into the cell nucleus, where it initiates the transcription of genes which causes an uncontrolled cleavage. Kern et al. (2006, Modulation of Key Elements of the Wnt-Pathway by Apple Polyphenols, J. Agric. Food. Chem., 54, 7041 to 7046) could show that the level of intracellular β-catenin in colon cancer cells cultivated in vitro was reduced by administration of apple juice.

Furthermore, it was found that apple show a large antioxidative activity and can increase the antioxidative capacity in blood (Rezk et al., 2002, The Antioxidant Activity of Phloretin: The Disclosure of a new Antioxidant Pharmacophore in Flavonoids, Biochem. Biophys. Res. Commun., 295, 9 to 13; Lee et al., 2003, Major Phenolics in Apple and their Contribution to the Total Antioxidant Capacity, J. Agric. Food Chem., 51, 6516 to 6520; Vrohovsek et al., 2004, Quantitation of Polyphenols in Different Apple Varieties, J. Agric. Food Chem., 52, 6532 to 6538; Lotito et al., 2004, Relevance of Apple Polyphenols as Antioxidants in Human Plasma: Contrasting in-vitro and in-vivo Effects, Free Rad. Biol. Med., 36, 201 to 211; Bitsch et al., 2000, Bioavailability of Antioxidative Compounds from Brettacher Apple Juice in Humans, Food Sci. Emerg. Technol., 1, 245 to 249). For this reason, apples are very interesting for establishing a dedifferentiated cell culture and its subsequent use in cosmetic preparations.

Dedifferentiated plant cells have a complex matrix of constituents of salts, acids, polyphenols, sugars, fats, proteins and other components. In addition to known components there is an unknown fraction of components which possibly is very valuable for cosmetic applications. It is known that raw plant extracts often show a better effect than identified and isolated individual components. Therefore, it is reasonable to use the entire cell lysate for application.

In order to obtain such total fraction of all ingredients special techniques are required since part of them are water-soluble whereas another part is fat-soluble. It was proposed to process plant cell culture preparations by means of lyophilization (e.g. WO2005072697, US20050265953). Thereafter, these lyophilized cells were pulverized and used in topic preparations.

Since transport of materials through the skin barrier is very limited, the technique of producing liposomes for many cosmetic applications was developed (e.g. KR20050091162, KR920005639B, GB2415375, WO2004067012, EP1498420, US2002160064, AU2388099). Application of this technique allows a better penetration of substances into the lower skin laminas. Also, a further advantage of liposomes is the encapsulation of fat-soluble ingredients in the membrane and thus their dispersion in aqueous phases.

There are various methods of liposome production. Main steps of their production comprise dissolving a phospholipid mixture in a suitable solvent (e.g. glycerol or alcohol), intermixing the dissolved lipids with an aqueous phase, applying energy (e.g. by stirring, shaking, pressure or heat) for forming the liposomes. As said above, the form of energy can by pressure. Formation of liposomes by means of high pressure homogenization is a known technique. Examples for pharmaceutical or cosmetic preparations may be found e.g. in WO9949716, NZ502840 or EP0782847. Interestingly the same technique can be used for solubilizing cells and obtaining their lysate (e.g. DE19918619). Therefore, it is possible to solubilize plant cells of suspension cultures and at the same time to extract the oil- and water-soluble agents into empty liposomes. Thereby, stability of the agents and their transportation into the skin can be improved.

From the above mentioned publication WO 2005/072697 A1 it is known to use lyophilizates of dedifferentiated plant cells for depigmenting the skin. This technique calls for the use of lyophilizates of dedifferentiated plant cells, in particular of cells of halophile plants. A use for stimulation and protection of skin stem cells is not envisaged.

From the publication EP 1,174,120 A1 it is known to use extracts, in particular of lyophilizates, of dedifferentiated cells of plants of the family Iridaceae (Iris-family) for stimulating immunity. Other plants or uses are not proposed.

The publication EP 1,064,932 A1 proposes the use of extracts of dedifferentiated plant cells in deodorants. Other uses are not disclosed.

The publication WO 03/077881 A discloses the use of lysates of metabolites of dedifferentiated cells of vine, which were obtained by means of a complicated method, for the preparation of cosmetics. This technique calls for the use of lyophilizates. A use for stimulation and protection of skin stem cells is not envisaged. Furthermore, other species of plants are not disclosed.

Furthermore, the publication WO 01/47538 A1 discloses the use of extracts of dedifferentiated cells of plants of the genus *Leontopodium* (Edelweiss) as UV filter. Other uses or other plants are not proposed.

OBJECTS OF THE INVENTION

The main object of the present invention is to create a cosmetic preparation which protects stem cells against intrinsic and extrinsic stress factors, in particular promotes the proliferation of stem cells and protects them against apoptosis.

Another object of the present invention is to provide a method for preparing an extract suitable for use in said cosmetic preparation.

SUMMARY OF THE INVENTION

The abovementioned object is achieved by using an extract of a suspension of dedifferentiated plant cells, preferably of the family of Rosaceae (Rose family), particularly of the subfamily Maloidae (Pome fruit), and more in particular of *Malus domestica* cultivar *Uttwiler Spaetlauber*, which is an old and rare kind of apple.

The method of preparing suitable extracts comprises the following main steps:
(a) Establishing a stable dedifferentiated cell line on a laboratory scale;
(b) Mass cultivation of the cells in an one-way bag reactor system (so-called Wave reactor), and
(c) Recovery of a total-extract by means of high pressure homogenization using empty liposomes.

Advantageously, in step (c) the following procedure is followed:
Decomposition of the plant cells by high pressure homogenization;
Extraction and stabilization of the substances of content by means of liposomes; whereby both steps are simultaneously performed as one single step.

BRIEF DESCRIPTION OF DRAWINGS

In the annexed drawings.

In FIGS. 2 and 4 "OD" is the abbreviation of "optical density".

DETAILED DESCRIPTION OF THE INVENTION

Figure 1:
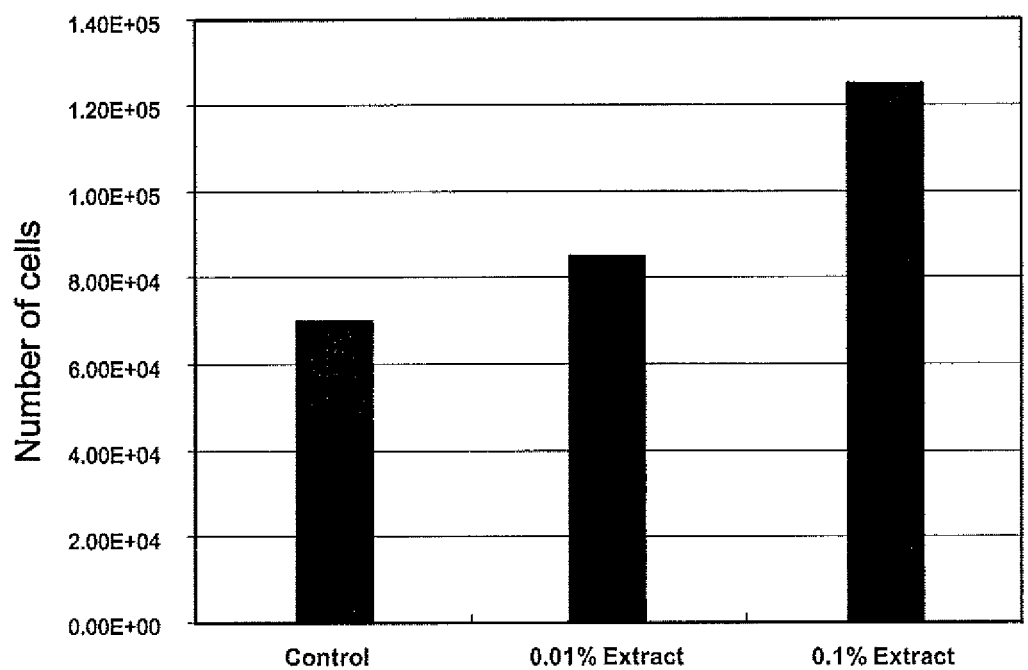
FIG. 1 shows the increase in the cell count of umbilical cord stem cells in dependence of different concentrations of a liposomal extract originating from dedifferentiated cells of apples of the cultivar *Uttwiler Spaetlauber*. For this study, the extract was centrifuged and sterilized by filtration.

Induction and Stabilization of Cell Line (a)
The following steps provide a dedifferentiated cell line from plant tissue:
(a1)) Choice of a suitable tissue for the induction.
(a2) Surface sterilization.
(a3) Cladding of the explanates on a suitable solid medium for callus induction.
(a4) Harvesting the callus grown on the injured surface of the explanates.
(a5) Sub-cultivation of the obtained callus on the same medium until the cells are entirely dedifferentiated.
(a6) Addition of the dedifferentiated cells to a suitable liquid medium.
(a7) Homogenization of the cells in suspension until big cell clump are no longer present; and
(a8) Sub-cultivation and continuous characterization of the cell suspension.

Fundamental working protocols for plant cell cultures can be found in the standard literature (e.g. Plant Cell Culture: A Practical Approach, Editor P. A. Dixon, 1994, Oxford University Press). Protocols for the work and suitable media for initiating plant cell cultures of apples are described by Nitsch et al., 1970, Bases physiologiques de la production de chair de pomme et de poire in vitro, Bull. Soc. Bot. Fr., 117, 479 to 492; und Pech et al., 1975, Croissance in vitro de tissues et de suspensions cellulaires de pomme, Bull. Soc. Bot. Fr., 122, 183 to 194. According to these protocols, initiating and maintaining such cultures should not present a problem.

Biomass Production (b)
In the following process, the obtained suspension culture is cultivated further over several continuous steps from small laboratory flasks (Erlenmeyer flask usually having 200 ml content) to production scale of 50 to 100 liters. In this process, 5 to 10 percent, preferably 10 percent, of the next culture volume of a fully grown cell suspension is used as inoculum. The scale-up may be done in steps of e.g. 0.1/1/10/100 liter.

Cultivation volumes exceeding 1 liter necessitate the use of special bioreactors instead of culture flasks used before. Many different systems are available on the market. Execution of cultivation is done, but is not limited thereto, in agitation reactors, bubble columns, loop reactors or newly developed one-way systems suitable for plant cell cultivation. For all these cultures the influence of shearing stress which can damage the cultures. Thus, the most important parameter for selecting a suitable reactor system usually is the manner how the culture is homogenized.

Moreover, control of the culture is very important. In comparison to cultures of yeast or bacteria, measurement of the biomass is difficult, and the growth of biomass has to be measured by means of indirect parameters, such as e.g. consumption of carbon, dropping of conductivity or the pH value or the increase of optical density. Once such a control is established, the end point or the harvest moment, respectively, can be fixed.

Also important is examination analysis of secondary metabolites which are characteristic for the cell culture. Measurement of such materials can be done by HPLC-VIS/UV/MC, LC, GC-MS, e.g. enzymatically or optically. Thereby, the stable and continuous expression of such metabolites during the whole process is decisive.

Biomass Processing (c)

In order to obtain an extract containing the whole essence of the cultivated cells, the cells are solubilized by means of liposomes. The main component of this method is the use of high pressure homogenization of the whole cell broth together with a liposome preparation. The great advantage of this method is its simple and low-cost application.

In detail, the method comprises the following steps:
(c1) Addition of a suitable liposome preparation to the cell broth;
(c2) Addition of a suitable preservative agent;
(c3) Addition of suitable antioxidants;
(c4) Mixing the substances; and
(c5) High pressure homogenization.

All preservative agents of natural or synthetic origin allowed for cosmetics, such as e.g. phenoxyethanol, benzoic acid, propionic acid, alcohol or silver chloride, can be used as preservative agents.

In order to additionally protect the extract from oxidation, antioxidants, such as e.g. ascorbic acid or tocopherol, may be added.

The described method allows the addition of still further substances useful in the preparation or cosmetic product. Once all compounds are added, the mixture has to be stirred in order to dissolve the preservative agents and other components. This may be done e.g. by means of a paddle mixer, a homogenization rod or by pumping through static mixing elements.

The subsequent high pressure homogenization pursues to objects:
Destruction of the cell membranes in order to release extractable substances; and
Generation of finely dispersed liposomes contained the fat- and water-soluble fractions of the cells.

Suitable high pressure homogenizers are commercially available on the market. The principle of the reaction chamber has to be selected from different possibilities and has to be previously tested. The number of passages through the reaction chamber necessary for a disintegration of all cell membranes or reaching a desired homogeneity of the extract has to be tested as well.

Afterwards, the extract obtained in this manner can directly be incorporated into cosmetic preparations, such as e.g. creams, soaps, lotions, gels or hair seras. If the extract is to be used as semi-finished good a supplemental thickening is possible. All thickening agents of natural or synthetic origin allowed for cosmetics can be used as thickening agents.

EXAMPLES

Example 1

Production of a Dedifferentiated Plant Cell Culture

Mature apples of the cultivar *Uttwiler Spaetlauber* were rinsed with tap water. In cylindrical pieces of a diameter of about one centimeter diameter the score was out along the axis of the by means of a cork borer. For the surface sterilization, the cylinders were dipped for 30 seconds into 70 percent ethanol and thereafter for 10 minutes into 2.5 percent sodium hypochloride containing 0.1 percent of the surfactant Tween 40. Thereafter, the sterilized cylinders washed tree times with distilled water, cut into slices of about 3 millimeter thickness, and placed on a solid medium of the following composition per liter:

| | |
|---|---:|
| Calcium chloride | 332 mg |
| Potassium dihydrogen phosphate | 170 mg |
| Potassium nitrate | 1900 mg |
| Magnesium sulfate | 180.54 mg |
| Ammonium nitrate | 1650 mg |
| Cobalt chloride hexahydrate | 0.025 mg |
| Copper sulfate pentahydrate | 0.025 mg |
| Iron-Sodium-EDTA | 36.7 mg |
| Boric acid | 6.2 mg |
| Potassium iodide | 83 mg |
| Manganese sulfate hydrate | 16.9 mg |
| Disodium molybdate dihydrate | 0.25 mg |
| Zinc sulfate heptahydrate | 8.6 mg |
| myo-Inositol | 100 mg |
| Nicotinic acid | 5 mg |
| Glycine | 2 mg |
| Pyridoxine hydrochloride | 0.5 mg |
| Thiamidine hydrochloride | 0.5 mg |
| Folic acid | 0.5 mg |
| Biotin | 0.05 mg |
| Ascorbic acid | 50 mg |
| Thiourea | 25 mg |
| L-Asparagine | 180 mg |
| Saccharose | 30000 mg |

The ph-value was adjusted to 5.6 with sodium hydroxide solution. Agar was added in a concentration of 0.8 percent as gelling agent. All ingredients were mixed together and sterilized at 121° centigrade for 15 minutes.

The induction of the primary callus was carried out in the dark at 25° centigrade. The formed calluses were harvested after two to three weeks and further incubated on the same medium. Several sub-cultivations were carried out until the callus was fully dedifferentiated.

Example 2

Production of a Suspension Culture

Dedifferentiated cell clumps growing on said solid medium were taken, homogenized and placed into the same medium without gelling agent. A finely dispersed suspension was obtained which could be use for larger cultivation systems. The suspensions were grown in the dark at 25 centigrade and a shaking velocity of about 100 rpm.

Example 3

Outbreak

One tenth of a fully grown culture (percentage of cells being about 50 percent of the total weight of the culture) was used for the seeding of the next volume step. The scale-up was effected in a one-way bag reactor system of Wave Biotech AG, Tagelswangen, Switzerland (so-called Wave Reactor). The scale-up was effected in steps of 1/10/25 liter. The temperature was held at 25 centigrade and the aeration at about 0.1 vvm. Various mixing speeds were applied in dependence of the bags used. Cultivation was carried out in the dark, and it took about 20 days until a bag was completely grownup.

Example 4

Preparation of a Liposomal Extract

After cultivation, the whole cell broth was mixed with a dispersion containing empty liposomes of a size of about 50 nanometer. The mixture was then four times high pressure homogenized at a pressure of about 1200 bar ($1.2*10^8$ N m$^{-2}$) resulting in a finely dispersed extract.

Example 5

Vanishing Cream

The percentage refers to the total quantity (weight/weight).

| | | |
|---|---|---|
| Oily phase 1: | Alkyl benzoates | 10% |
| | Dimeticone | 3% |
| | Archidyl glycosides | 3% |
| | Myristyl glycoside | 2% |
| Oily phase 2: | Polyacrylamides | 1% |
| Aqueous phase: | Demineralized water | 71% |
| | Glycerol | 5% |
| | Phenoxyethanol | 1% |

Oily phase 1 and the aqueous phase were heated at 80 centigrade and blended. The mixture was chilled to 60 centigrade. Then oily phase 2 was added, and the mixture was blended. The mixture was chilled to 30 centigrade. 4 percent of the extract described in Example 4 was added and the mixture was blended again.

Example 6

Liquid Balm for the Scalp

The percentage refers to the total quantity (weight/weight).

| | |
|---|---|
| Ethanol | 0.5% |
| Urea | 5% |
| Propylene glycol | 0.5% |
| Carbomer | 0.4% |
| Bisabololene | 0.1% |
| PEG-60 | 0.6% |
| D-Panthenol 75% | 0.5% |
| Sodium hydroxide 30% | 0.4% |
| Plant cell extract of Example 4 | 1% |
| Water | filling up to 100% |

Example 7

Intensive Hair Mask

The percentage refers to the total quantity (weight/weight).

| Phase | Ingredient | Amount |
|---|---|---|
| Aqueous phase 1 (W1) | Water | filling up to 100% |
| | Citric acid | 0.6% |
| | Sodium benzoate | 0.5% |
| Aqueous phase 2 (W2) | D-Panthenol 75% | 0.7% |
| Oily phase 1 (O1) | Cetearyl alcohol | 4.5% |
| | Dicocoylethyl hydroxyethlmonium methosulfate | 3% |
| | Distearoylethyl hydroxetylmonium methosulfate | 1.5% |
| | Dicapryryl ether | 1% |
| | Gycerol stearate | 1% |
| Oily phase 2 (O2) | Amino dimethicone | 0.3% |
| Plant extract (A) | Pant cell extract of Example 4 | 2% |

Instruction for Preparation

Aqueous phase 1 is mixed and heated to 75 centigrade. Shortly before mixing with oily phase 2 aqueous phase 2 (panthenol) is added. Oily phase 1 is heated to 75 centigrade, and shortly before mixing oily phase 2 (aminodimethicone) is added. The combined aqueous and oily phases are mixed and homogenized. The mixture is chilled to 30 centigrade, and phase A (plant extract) is added.

Example 8

Eye Cream

The percentage refers to the total quantity (weight/weight).

| Phase | Ingredient | Amount |
|---|---|---|
| Aqueous phase 1 (W1) | Water | filling up to 100% |
| | Citric acid | 0.6% |
| | Glycerol | 5% |
| | Butylene glycol | 5% |
| | Galacto arabinane | 0.3% |
| | Parabens in phenoxyethanol | 0.8% |
| Oily phase 1 (O1) | Polyglyceryl-3-methylglucose distearate | 2.5% |
| | Hydrogenated polyisobutene | 3% |
| | Vegetable oil | 4% |
| | Dicapryryl ether | 3% |
| | Behenyl alcohol | 2% |
| | Dimethicone | 0.5% |
| Oily phase 2 (O2) | Maize phosphates | 1% |
| | Dimethicone | 0.5% |
| Plant extract (A) | Plant cell extract of Example 4 | 2% |

Instruction for Preparation

Aqueous phase is mixed and heated to 80 centigrade. Oily phase 1 is heated to 80 centigrade, and oily phase 2 is added. The combined aqueous and oily phases are mixed and homogenized. The mixture is chilled to 30 centigrade, and phase A (plant extract) is added, and the blend is mixed again.

Example 9

In-Vitro-Test on Stem Cells

The test was carried out on stem cells originating from the umbilical cord. The cells were grown in a complex medium containing 10 percent of fetal calf serum. The supernatant without cell debris was used for the test. Previous to the test, the extract was sterilized by filtration.

Figure 3:
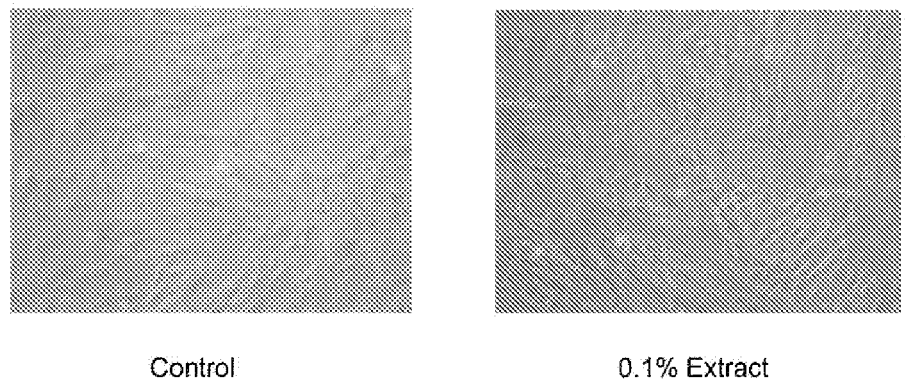
FIG. 3 shows microscopic pictures of umbilical cord stem cells. The left photograph shows cells cultivated in a medium without extract, the right photograph cells cultivated together with 0.1 percent of a liposomal extract originating from dedifferentiated cells of apples of the cultivar *Uttwiler Spaetlauber*. For this study, the extract was centrifuged and sterilized by filtration.

The addition of 0.1 percent of the extract resulted in a increase of the cell count of about 44 percent (FIGS. 1 and 3).

Figure 2:
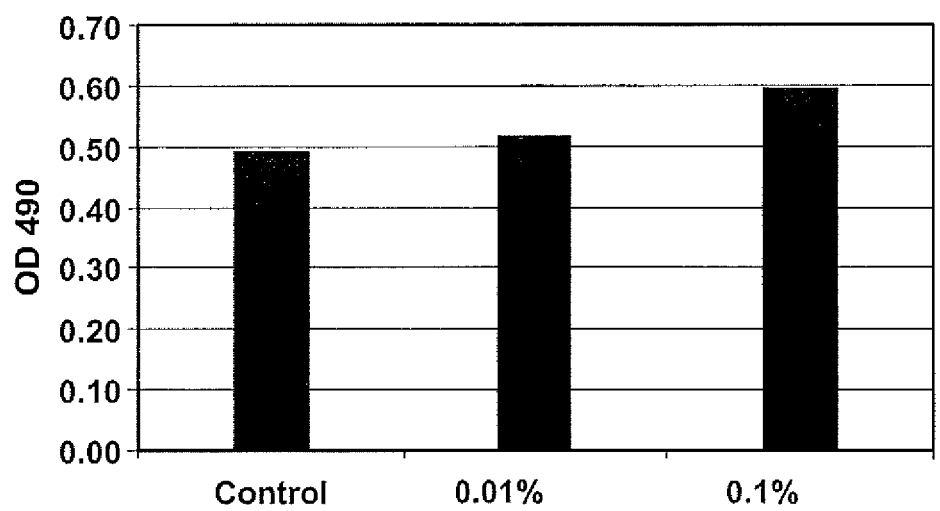
FIG. 2 shows the increase in proliferation capability in a MTS-assay of umbilical cord stem cells in dependence of different concentrations of a liposomal extract originating from dedifferentiated cells of apples of the cultivar *Uttwiler Spaetlauber*. For this study, the extract was centrifuged and sterilized by filtration.

Also, in a subsequent MTS-assay on addition of 0.1 percent of the extract an increase of the proliferation capability of the cells of 20 percent could be verified (FIG. 2).

Figure 4:
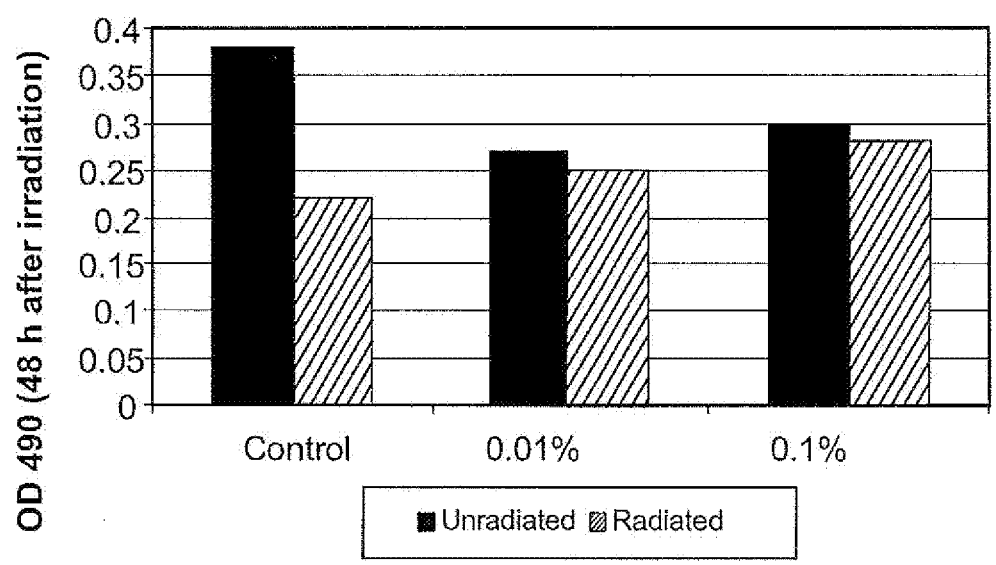
FIG. 4 shows the proliferation capability of umbilical cord stem cells of a control preparation and of a liposomal extract of different concentrations originating from dedifferentiated cells of apples of the cultivar *Uttwiler Spaetlauber*, 48 hours after UV irradiation. For this study, the extract was centrifuged and sterilized by filtration.

In addition to said growth and proliferation studies umbilical cord cells together with a liposomal extract of dedifferentiated cells of Apples of the cultivar *Uttwiler Spaetlauber* were tested for the effects of UV radiation. Application of 0.1 percent of extract resulted in a reduction of the proliferation capability of about 7 percent, whereas the control preparation showed a loss of proliferation capability of 42 percent (FIG. 4).

Example 10

Ex-Vivo-Test on Isolated Hair Follicles

The epithelium of the hair root bulges into a suprabasal bulge which is the niche of the ceratinozyte stem cells. They consist of clonal subpopulations which regenerate skin and hair follicles. Thus, isolated hair follicles are a suitable model for analyzing the life expectancy of stem cells.

Hair follicles were isolated from skin material originating from an esthetic surgery. Then they were placed in a nutrient solution where they lived and started growing. In this manner, hair follicles could be kept alive for about 14 days. Thereafter, the cells begin to die off, and the newly formed hair begins to shrink, a control assay of 12 follicles was incubated in the nutrient solution only. Whereas a second series was incubated in a nutrient solution containing 0.2 percent of a liposomal extract of dedifferentiated cells of apples of the cultivar Uttwiler Spaetlauber. On the 16th, 18th and 20th day the length of the hair follicles was measured.

The ex vivo test showed that, as excepted, the follicles of the control assay had lost about 6 percent of its length already on the 16th day. A similar shrinking could be asserted on the 18th day. Then, on the 20th day a considerable dying of 52 percent was measurable. The follicles treated with the extract remained longer in the growth phase. On the 16th day, an increase in length of 8 percent could still be measured. Not until the 18th day a slight shrinking arose. The dying on the 20th day was clearly lesser than in the control assay.

Figure 5:
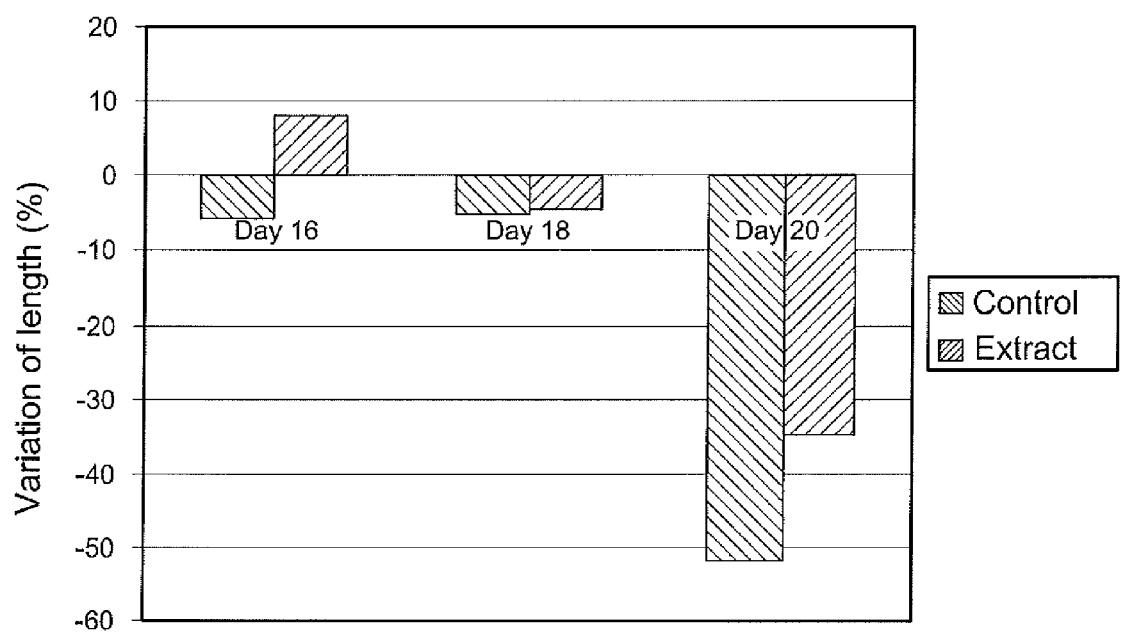
FIG. 5 shows the temporal influence of a liposomal extract according to Example 10 on the length of hair follicles.

In detail, the following variations in length were detected. They are graphically represented in FIG. 5.

|  | Control | Extract |
| --- | --- | --- |
| 16th day | −5.7% | 7.8% |
| 18th day | −5.3% | −4.8% |
| 20th day | −52% | −35% |

Thus, Example 10 shows that a liposomal extract of dedifferentiated cells of apples of the cultivar Uttwiler Spaetlauber is able to prolong the expectancy of life of ceratinocyte stem cells.

Dermatologic Tests

Test 1
Anti-Wrinkle Effect of PhytoCellTec™ Malus Domestica

The following dermatological test was carried out by Dr. H. P. Nissen, of Derma Consult GmbH, D-53347 Alfter, Germany. PhytoCellTec∩ Malus Domestica is the Applicant's Trade Mark for products prepared in accordance with the present invention.

Figure 6:
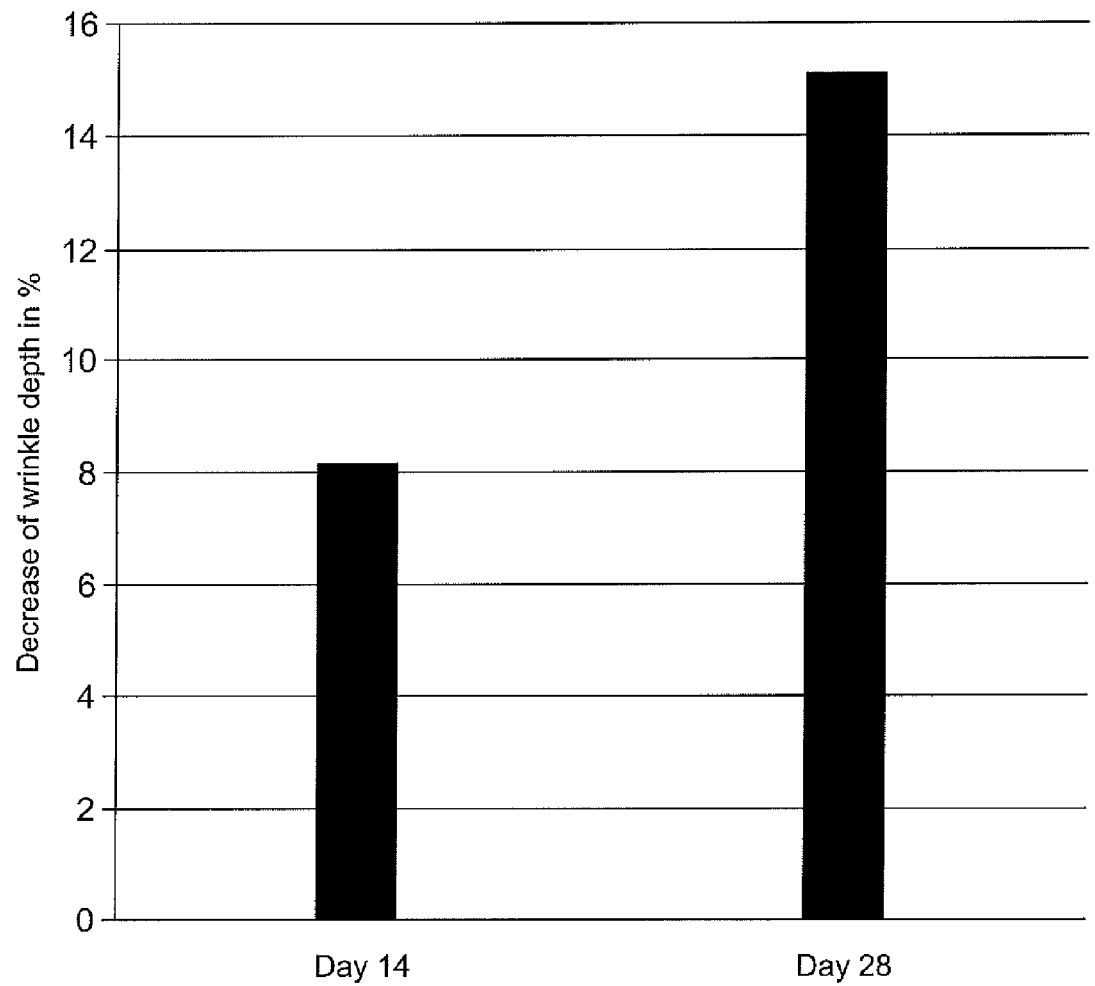
FIG. 6 shows the effect of a preparation in accordance with the present invention as anti-wrinkle cream in Test 1 described hereafter.
Figure 7:
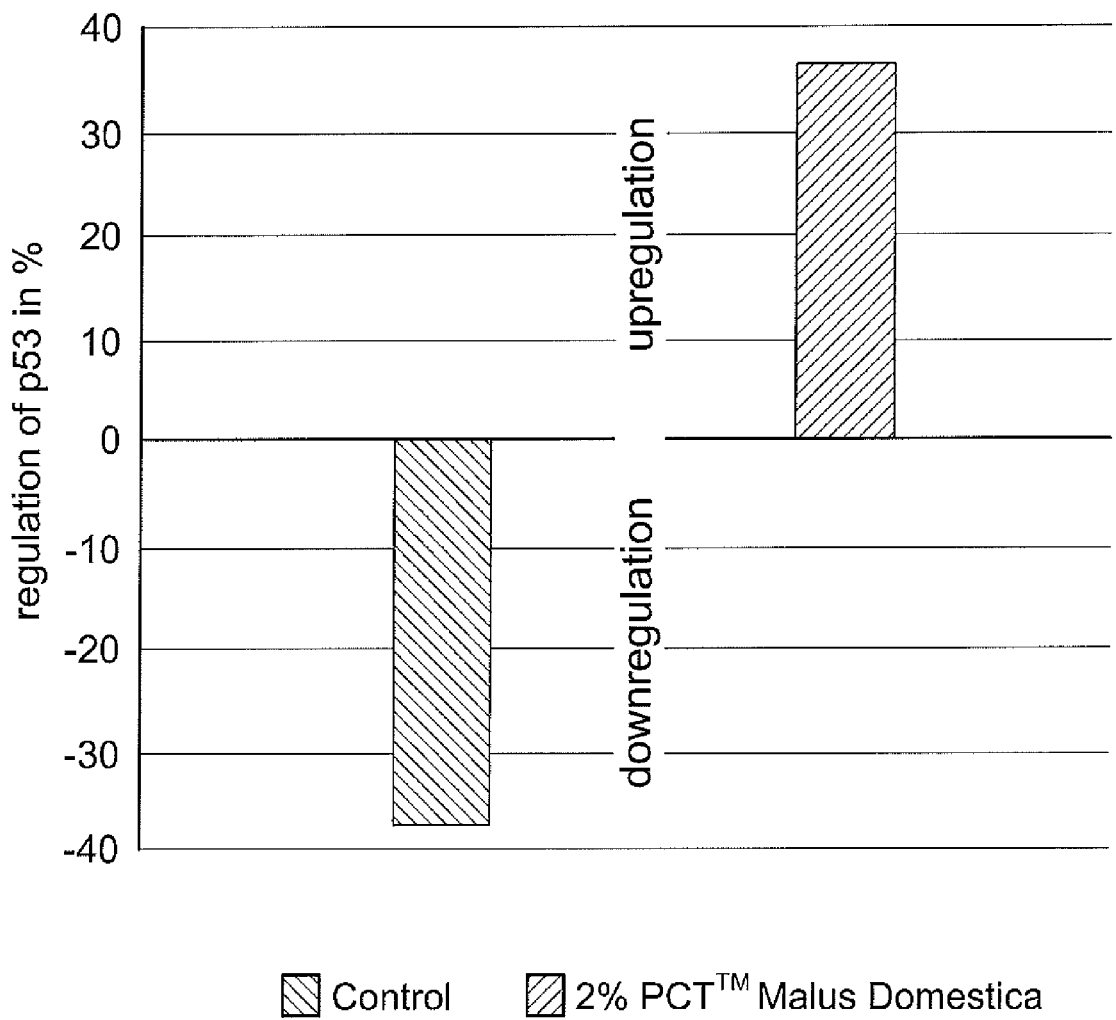
FIG. 7 shows the effect of a preparation in accordance with the present invention on stressed skin in Test 2 described hereafter.

Test Product
Cream containing 2.0% of PhytoCellTec™ Malus Domestica
Test area
Crow's feet area
Volunteers
Number of individuals: 20
Age: 37 to 64 years
Sex: female
Application
Duration: 28 days
Frequency: twice daily
Test Parameter
Wrinkle depth by means of an apparatus PRIMOS® 5.5 of GFMesstechnik GmbH, D-14513 Teltow, Germany
Study Design
Day 0
 Determination of the test parameter in the test areas; first application of the test product
Day 1 to 13
 Application of the test product twice a day
Day 14
 Determination of the test parameter 8 to 12 hours after the last daily test product application
Day 15 to 27:
 Application of the test product twice a day
Day 28:
 Determination of test parameter 8 to 12 hours after the last daily test product application
Results
Two daily applications of the test cream containing 2% of PhytoCellTec™ Malus Domestica over 28 days resulted in a significant decrease in wrinkle depth in all of the volunteers tested. These results are represented in FIG. 6.
Test 2
Effect of PhytoCellTec™ Malus Domestica on Stressed Skin The following dermatological test was carried out by F. Juchaux, of BIOalternatives, F-86160, France. PhytoCellTec™ Malus Domestica is the Applicant's Trade Mark for products prepared in accordance with the present invention.
Introduction In normal skin the tumor suppressor gene p53 is upregulated by several types of stress, e.g. DNA damage (induced by UV radiation, IR radiation, or chemical agents, such as hydrogen peroxide), oxidative stress, or osmotic shock. The protein p53 plays an important role in the cell cycle as transcription regulator. In old skin this gene is no more upregulated but rather down regulated by stress.
Test Product
 2.0% of PhytoCellTec™ Malus Domestica
Cells
 Normal human dermal fibroblasts (NHDF) used at 10th passage
Procedure Fibroblasts were stressed for 2 hours with culture medium containing 600 µmole of $H_2O_2$. For recovery, the cells were incubated for 72 hours with a medium containing, or not containing (control), 2% of PhytoCellTec™ Malus Domestica. After the incubation time, mRNA was extracted and transcribed into $^{33}$P-labeled cDNA via reverse-transcription. These labeled cDNA targets were hybridized to an "old skin" specific minichip. This minichip contained about 150 genes specific for skin aging. The content of labeled genes on the minichip was measured.
Results In $H_2O_2$-stressed fibroblasts, p53 was downregulated. $H_2O_2$-stressed cells treated with 2% PhytoCellTec™ Malus Domestica showed an upregulation of p53. These results are represented in FIG. 7.

What is claimed is:

1. A cosmetic preparation comprising:
  a dermatologically suitable carrier suitable for topical application to a human body, and
  an active component dispersed throughout the carrier, wherein the active component comprises a whole cell lysate of dedifferentiated Malus domestica cells encapsulated and stabilized in finely dispersed liposomes of a size of about 50 nm.

2. The cosmetic preparation as set forth in claim 1, comprising 0.01 to 90 percent by weight of the active component relative to the carrier.

3. The cosmetic preparation as set forth in claim 2, comprising 0.1 to 10 percent by weight of the active component relative to the carrier.

4. The cosmetic preparation as set forth in claim 1, wherein the encapsulated and stabilized whole cell lysate is obtained by homogenizing cultured dedifferentiated whole cells of *Malus domestica* in the presence of said liposomes at a pressure of about 1200 bar.

5. The cosmetic preparation as set forth in claim 1, wherein the cosmetic preparation further comprises pharmaceutically and cosmetically compatible preservative agents and antioxidants.

6. The cosmetic preparation as set forth in claim 1, wherein the cosmetic preparation is provided in creams, soaps, lotions, gels or hair serum.

\* \* \* \* \*